United States Patent [19]
O'Brien

[11] Patent Number: 5,616,872
[45] Date of Patent: Apr. 1, 1997

[54] PARTICLE SIZE AND CHARGE MEASUREMENT IN MULTI-COMPONENT COLLOIDS

[75] Inventor: Richard W. O'Brien, Turramurra, Australia

[73] Assignee: Colloidal Dynamics PTY LTD, Sydney, Australia

[21] Appl. No.: 513,934

[22] PCT Filed: Jun. 7, 1994

[86] PCT No.: PCT/AU94/00307

§ 371 Date: Aug. 31, 1995

§ 102(e) Date: Aug. 31, 1995

[87] PCT Pub. No.: WO94/29694

PCT Pub. Date: Dec. 22, 1994

[30] Foreign Application Priority Data

Jun. 7, 1993 [AU] Australia .................. PL9250

[51] Int. Cl.[6] ............... G01N 15/02; G01N 15/00; G01N 29/02; G01R 29/24
[52] U.S. Cl. ............... 73/865.5; 73/61.75; 73/587; 324/457; 324/453; 324/71.1
[58] Field of Search ............... 73/865.5, 28.02, 73/61.42, 61.75, 61.79, 64.53, 64.42, 587, 61.66; 324/457, 453, 71.1, 452

[56] References Cited
U.S. PATENT DOCUMENTS

| | | | |
|---|---|---|---|
| 4,552,019 | 11/1985 | Freeman | 73/584 |
| 4,602,989 | 7/1986 | Culkin | 204/180.1 |
| 4,674,337 | 6/1987 | Jonas | 73/61.75 X |
| 4,679,439 | 7/1987 | Culkin | 73/61.66 |
| 4,907,453 | 3/1990 | Marlow et al. | 73/61.79 X |
| 5,121,629 | 6/1992 | Alba | 73/865.5 X |
| 5,245,290 | 9/1993 | Cannon et al. | 73/865.5 X |

FOREIGN PATENT DOCUMENTS 129766 1/1985 European Pat. Off.
WO88/02482 4/1988 WIPO.

Primary Examiner—Thomas P. Noland
Attorney, Agent, or Firm—Kinney & Lange

[57] ABSTRACT

A method and device is disclosed for determining the distribution of charge and size in a colloidal system. The arrangement disclosed is adapted to measure these characteristics in an inhomogeneous colloid. A colloid is subjected to a steady or slowly varying force which moves the particles at a rate that depends on their radius or charge and thereby sets up spatial inhomogeneities in the suspension, and to either a unsteady mechanical force or an unsteady electrical force, and the resulting electrical or acoustic effects sensed. Monitoring these characteristics over time and subsequent calculation allows the determination of charge and size distribution, for each species present.

23 Claims, 1 Drawing Sheet ed by the pa

PARTICLE SIZE AND CHARGE MEASUREMENT IN MULTI-COMPONENT COLLOIDS

FIELD OF THE INVENTION

The present invention relates to a method and means for determining the distribution of particle size and charge in a colloidal system.

BACKGROUND ART

A colloid is a suspension of small particles suspended in a fluid. Although the fluid may be a gas or a liquid, the present invention relates to suspensions of particles in a liquid. The particles may be solid, or they may be emulsion droplets. For more details of the properties of colloids, the reader is referred to the text "Foundations of Colloid Science" by R J Hunter (Oxford Press 1987).

Colloidal particles nearly all carry an electric charge. The charge, which usually resides on the particle surface, can arise from a number of mechanisms including dissociation of acidic or basic groups on the surface or by the adsorption of ions from the surrounding liquid. This charge is balanced by an equal and opposite charge in the liquid. These opposite charges form a diffuse cloud around the particle. The voltage drop between the particle surface and the liquid outside this cloud is called the "zeta potential", denoted by the symbol $\zeta$. The invention described is intended to measure the $\zeta$ potential and from that quantity the surface charge can be calculated (see e.g chapter 2 of "Zeta Potential in Colloid Science" by R. J. Hunter, Academic Press, 1981).

Colloids have many applications in industries ranging from coatings and ceramics to pharmaceuticals and food processing. In many of these applications the efficiency of the process or the quality of the end-product depends crucially on the $\zeta$ potential and size of the colloidal particles.

Known methods for determining particle size include electron microscopes, Coulter Counters, centrifuges and dynamic light scattering devices. Each of these devices suffers from the drawback that they can only deal with suspensions in which the particles are of a uniform composition. Thus they would not be able to determine the individual size distribution within a colloid of a mixture of titania and silica particles for example.

These techniques also suffer from the drawback that they do not determine the $\zeta$ potential of the particles.

In U.S. Pat. No. 5,059,909 "Determination of Particle Size and Charge" to the present applicant there is described a method for determining both size and $\zeta$ potential from "electroacoustic" measurements, that is measurements of the sound waves generated by applied electric fields or measurements of the voltages and electric currents generated by applied sound waves in the colloid. In the analysis provided in this patent it is assumed that the suspension is macroscopically homogeneous, and this technique is limited to particles of uniform composition. It is also implicitly assumed that the particles all have the same $\zeta$ potential. The technique disclosed is limited to the use of at least 2 different frequencies in the applied fields. The phenomenon of sound wave generation by an applied electric field is called the Electrokinetic Sonic Amplitude (ESA) effect and is described in U.S. Pat. No. 4,497,208 to Oja et al. The reverse effect of electric field generated by an applied sound wave is termed the "Colloid Vibration Potential" or CVP, and has been described in the scientific literature (see for example the review article "Ultrasonic vibration potentials" Zana R. and Yaeger E. B. in *Modern Aspects of Electrochemistry*, vol 14. Plenum). All the techniques described above are limited to particles of uniform composition.

It is an object of the present invention to provide a method and device capable of measuring both size and charge distribution in at least dilute mixed particle colloids.

SUMMARY OF THE INVENTION

According to one aspect the present invention provides a method for determining the particle charge and size distribution of particles suspended in a fluid medium, said particles belonging to at least two different species, comprising the steps of:

subjecting the suspension to at least one steady, or slowly varying force which moves the particles at a rate that depends on their radius or charge and thereby sets up spatial inhomogeneities in the suspension;

applying at least one of an unsteady electric field and an unsteady mechanical force to the suspension to accelerate the particles;

measuring the resulting acoustic wave generated by the particles as a result of the application of the unsteady electric field, or the resulting electric response generated by the particles as a result of the application of unsteady mechanical force;

monitoring the change in these measurements with time due to the steady or slowly varying applied force; and calculating the particle size and/or charge distributions for the particles. According to another aspect the present invention provides a method for determining the particle charge and size distribution of particles suspended in a fluid medium comprising:

subjecting the suspension to at least one steady, or slowly varying force which moves the particles at a rate that depends on their radius or charge and thereby sets up spatial inhomogeneities in the suspension;

applying at least one of an unsteady electric field and an unsteady mechanical force to the suspension to accelerate the particles;

measuring the resulting acoustic wave generated by the particles as a result of the application of the unsteady electric field, or the resulting electric response generated by the particles as a result of the application of unsteady mechanical force;

monitoring the change in these measurements with time due to the evolution of the spatial inhomogeneities in the suspension; and calculating the particle size and/or charge distributions for the particles. The invention further encompasses devices for implementing the methods described above.

The present invention relates to a modification of the method described in the applicant's previous patent, U.S. Pat. No. 5059909, the disclosure of which is incorporated by reference. The present invention allows size and charge distributions to be determined in dilute suspensions containing mixtures of particles with different densities and $\zeta$ potentials.

Instead of making electroacoustic measurements on homogeneous suspensions as envisaged in the applicant's earlier patent, the present invention involves measurements on spatially inhomogeneous suspensions. The present technique does not require the use of 2 or more frequencies in the applied field, as in the applicant's earlier patent. The inhomogeneity can be caused by particle sedimentation under gravity or in a centrifugal field, by the electrophoretic motion of particles in a steady applied electric field, or by any effect which tends to separate particles according to $\zeta$ potential or size. The applied field causes the spatial distribution of the particles to change with time, and this leads to a corresponding change in the measured electroacoustic signal. If different species of particles are present in the colloid with sufficiently different properties under the applied field, the contribution of each can be separated. The present invention provides a method and means for extracting the zeta potentials and size distributions of the different particles from an analysis of the evolution of the electroacoustic signal with time.

BRIEF DESCRIPTION OF DRAWINGS

One embodiment of the invention will now be described with reference to the accompanying Figures, in which.

DETAILED DESCRIPTION

For convenience we will describe the present invention for the case when the ESA is the measured electroacoustic effect. The modifications for other electroacoustic measurements will be described at the end of the section. It will be apparent that other implementations are possible within the general scope of the invention as described below. In particular, other measurement techniques may be utilised if desired. It will further be appreciated that while the theoretical explanation is believed to be accurate, the present invention is not limited to the accuracy of the theoretical explanation provided.

Figure 1:
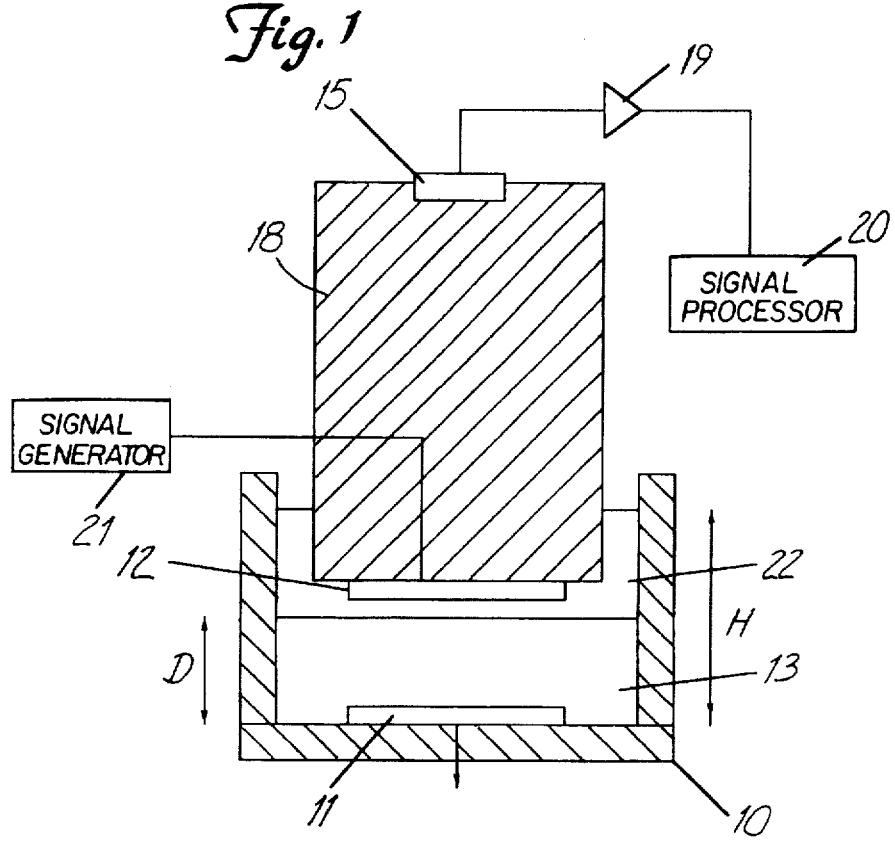
FIG. 1 illustrates schematically a suitable measurement cell.

Although the method described here can be applied to arbitrary device geometries we will illustrate the method for the simple case in which the electric field is applied across two horizontal electrodes, as shown in FIG. 1. In the illustrative measurement cell 10, the ESA is generated by a pulse of sinusoidal voltage from the signal generator 21. The top electrode 12 is attached to the bottom of a solid delay line 18. Delay line 18 is designed to introduce a delay between the application of the voltage pulse and the arrival of the ESA signal at the detecting transducer 15 on the top of delay line 18. In this way the ESA can be detected without any electrical interference from the applied voltage. It will be appreciated by the reader that this is a standard technique in pulse-echo ultrasonics (see for example U.S. Pat. No. 4497208 by Oja et al). The detecting transducer may be of any suitable type, for example formed from a piezoelectric material such as a lithium niobate crystal. If the instrument is required to be operated at a fixed frequency, the crystal can be cut to a thickness so as to resonate at that frequency, and thereby increase the transducer sensitivity. For this parallel plate configuration, the applied voltage leads to an electric field that is spatially uniform across the gap. We let E(t) denote this electric field. Although the particle distribution in the gap is changing with time, the duration of the applied voltage pulse is assumed to be much smaller than the time for the particle distribution to change significantly. Thus in calculating the ESA effect generated by an applied pulse we can take the particle distribution as fixed during the period of the pulse. The changes that occur in the distribution will cause the ESA signals to vary with each applied pulse, but this will occur over much longer time scales. Typical times for an applied voltage pulse would be 10 µs, while the spatial variations that we envisage would typically occur on time scales of a second or more.

To begin with we will consider the case of a suspension of particles of uniform composition and size. By solving the differential equations for the ESA sound wave field given in O'Brien's paper ("The electroacoustic equations for a colloidal suspension" Journal of Fluid Mechanics, 212, 81, 1990), we find that the applied voltage pulse generates a sound wave pressure at the top electrode given by $$p(t) = A \Delta \rho \int_0^\infty u\left(t - \frac{x}{c}\right) \frac{\partial \phi}{\partial x} dx \quad (1)$$

Here A is a device constant, $\Delta \rho$ is the particle density minus that of the liquid and $\phi(x)$ is the particle volume fraction (i.e the volume of particles per unit volume of suspension) at a distance x below the top electrode. The quantity u is the particle velocity due to the applied electric field. Since the field is spatially uniform, this velocity is the same for all particles in the gap at any instant. From the formula (1) it can be seen that the pressure is generated by spatial gradients in the particle concentration $\phi$. The contribution to the pressure from the particles at a distance x below the electrode involves the velocity u(t-x/c), that is the velocity at a time x/c earlier. The quantity c is the speed of sound in the liquid. The time delay x/c comes about because the pressure field from the particles a distance x below the electrodes propagates to the electrode at the speed of sound, and x/c is the time it takes for that sound wave to reach the top electrode.

The ESA sound waves passes through the electrode 12 and into the delay line 18, as shown in FIG. 1. In a practical device this pressure wave is preferably detected by transducer 15. As the sound wave strikes transducer 15 it generates a voltage signal that provides a measure of the pressure signal p(t). The detected signal is amplified by preamplifier 19, and processed by signal processor 20. As this is a common arrangement in pulse-echo ultrasonics, no detailed explanation of components will be provided as the technique is well understood by those skilled in the art.

As the particles sediment, a clear layer of liquid 22 develops adjacent top electrode 12, with a colloid layer 13 below. If the suspension is uniform to begin with, the particles below the liquid layer will also be spatially uniform. Thus the spatial derivative of $\phi$ will be zero in these regions and they will not contribute to the formula (1) for the pressure signal. At the top of the colloid layer 13 however there is a jump from zero concentration to a uniform value. Thus the spatial derivative of $\phi$ in this region is very large and so a pressure signal will be generated. Hence an ESA soundwave will emanate from the interface between the clear liquid 22 and colloid 13. There will also be a sound wave generated by the concentration gradients at the bottom electrode 11. This second signal will reach transducer 15 at a time D/c later than the first, where D is the distance from the bottom electrode 11 to the bottom of the clear liquid layer 22, as shown in FIG. 1. To keep the analysis simple, it will be assumed that the duration of the applied voltage pulse is less than this delay time. Thus the two pulses are separated in time. For the case of a 10 µs pulse this is the case if the delay D/c is greater than 10 µs. For a water based suspension the speed of sound is about 1500 ms$^{-1}$ and thus the height D of the clear liquid layer above the bottom of the cell must be more than 1.5 cm if the two pulses are to be separated in time. Thus, if the cell height is 10 cm, the two signals will be separated in time until the suspension has sedimented a distance of 8.5 cm. In the following discussion we will focus on the analysis of the first pulse, which arises from the boundary between the suspension and the clear liquid layer.

As the suspension sediments the delay between the applied voltage pulse and the transducer signal will increase at a rate proportional to the sedimentation velocity V of the particles. Thus the sedimentation velocity can be determined from measuring this delay as a function of time. The particle radius a can then be calculated from the sedimentation velocity. For example in the case of sedimentation under gravity the radius is given by (See e.g. equation (3.5.3) on p135 of "Foundations of Colloid Science" Vol 1., by R. J. Hunter, Clarendon Press, Oxford 1987)

$$a = \sqrt{\frac{9\rho v V}{2\Delta\rho g}} \quad (2)$$

where $\rho$ and $v$ are the density and kinematic viscosity of the liquid respectively and g is the gravitational acceleration.

Instead of calculating V from the delay in the signal however, it is more convenient, when it comes to complicated suspensions, to determine V from the Fourier Transform of the signal p(t). The Fourier Transform is a complex quantity denoted by $P(\omega)$, and defined by $$P(\omega) = \int_{-\infty}^{\infty} p(t) e^{-i\omega t} dt \quad (3)$$

It is well known that any pulse p(t) can be represented as a sum (or to be more precise, an integral) of "harmonics", that is, signals which vary sinusoidally with time. The quantity $P(\omega)$ represents the harmonic component of p(t) with frequency $\omega$. The advantage of working in terms of Fourier Transforms $P(\omega)$, rather than p(t) is that the theory for analysing the ESA signals assumes sinusoidal variations, and so the application of that theory to our problem is more straightforward when we work with Fourier Transforms. The signal processing circuits for determining the Fourier Transform of a signal are standard and will not be described here.

On multiplying both sides of equation(1) by $e^{-i\omega t}$ and integrating with respect to t we find that the Fourier Transform of the ESA pulse is given by $$P(\omega) = A\Phi\Delta\rho U(\omega) e^{-i\frac{\omega V t}{c}} \quad (4)$$

where $\Phi$ is the density of the particles below the clear liquid layer and $U(\omega)$ is the Fourier Transform of the particle velocity u(t) due to the applied voltage pulse. Thus $U(\omega)$ is the sinusoidal component of the particle velocity at frequency $\omega$. It can be shown that this component is proportional to the component $E(\omega)$ of the applied electric field at that frequency, that is $$U(\omega) = \mu_D(\omega) E(\omega) \quad (5)$$

The constant of proportionality $\mu_D$ is termed the "frequency-dependent electrophoretic mobility" or, more simply, the "dynamic mobility". From this definition it can be seen that the dynamic mobility is the particle velocity per unit electric field for the case of an alternating electric field.

The dynamic mobility is related to the size and zeta potential of the particle by the formula (O'Brien 1988 equation 6.11):

$$\mu_D = \frac{\epsilon \zeta}{\rho v} G\left(\frac{\omega a^2}{v}\right) \quad (6)$$

where $$G(\alpha) = \left[1 + \frac{\frac{i}{9}\alpha\left(3 + 2\frac{\Delta\rho}{\rho}\right)}{(1 + (1+i)\sqrt{\alpha/2})}\right]^{-1} \quad (7)$$

and $\epsilon$ is the permittivity of the suspending liquid. In the applicant's earlier patent, referred to above and incorporated herein by reference, it is shown how this formula can be used to determine the radius and $\omega$ potential from the dynamic mobility of the particle.

From the formula (4) for $P(\omega)$ it can be seen that the Fourier Transform of the ESA will vary sinusoidally with t as the suspension sediments. The frequency of this sinusoidal variation is $(\omega V)/c$. Thus the sedimentation velocity can be determined by measuring this frequency and from this the particle size can be ascertained. To give some idea of the size of this frequency, the gravitational sedimentation velocity of a 1 μm radius particle of density 2 gm/cc in water is 2 μm/s. Thus if the transform frequency $\omega$ is $2\pi*10^6 s^{-1}$ (a typical value), the "sedimentation" frequency $\omega V/c$ will be $0.01 s^{-1}$. Thus the variation in the ESA signal due to the sedimentation occurs on a much longer time scale than the duration of the applied pulse, as mentioned earlier. To obtain the frequency $\omega V/c$ of the sinusoidal variation it would be necessary to monitor the ESA signal for about 100s in this case.

Now we consider a more complicated suspension, in which the particles have a distribution of sizes, but still have a uniform density and $\omega$ potential. In this case different size particles will fall at different rates. For each size range there will be an interface formed and an ESA signal generated. The total ESA signal will be given by the sum of the signals from the particles in each size range:

$$P(\omega) = AE(\omega) \sum_j \phi_j \Delta\rho \mu_D(\omega)_j e^{-i\frac{\omega V_j t}{c}} \quad (8)$$

where the subscript j refers to the particles of size range j. In the case of a continuous distribution the sum in this formula would be replaced by an integral.

From the formula (8) it can be seen that $P(\omega)$ is made up of a sum of quantities which each vary sinusoidally with time. The frequencies and the amplitudes $\phi_j(\Delta\rho)\mu_{Dj}$ of the various components can be determined from a standard Fourier analysis of the signal for P as a function of time. From the frequency of each component the sedimentation velocity and size can be determined.

Since the size is known, we can evaluate the quantity G in the formula (7) for $\mu_D$ for each size. Thus from the measured amplitudes we can determine $\zeta\phi_j$ for each component. If the total volume fraction $\phi$ of the particles is known, we can then determine $\zeta$ and all the $\phi_j$'s by using the fact that $$\sum_j \phi_j = \phi \quad (9)$$

Thus the size distribution and the $\zeta$ potential can be determined from electroacoustic measurements on a suspension with particles of uniform composition.

To illustrate the application to a suspension is which the particles are not of uniform composition, consider the case of a suspension in which there are two types of particulate matter, one of density $\rho_1$ and the other of density $\rho_2$. The $\zeta$ potentials of the two species are $\zeta_1$ and $\zeta_2$ respectively.

The Fourier Transform of the signal in this case has the form $$P(\omega) = AE(\omega) \sum_j (\phi_j^1 \Delta\rho^1 \mu_{Dj}^1 + \phi_j^2 \Delta\rho^2 \mu_{Dj}^2) e^{-i\frac{\omega V_j t}{c}} \quad (10)$$

where we have grouped together the contributions from the components of the two species with the same sedimentation velocity. Since these species have different densities and the same sedimentation velocity they will have different radii. By the Fourier Analysis of the signal we find the frequency and amplitude of the various components as before, and from the frequency we determine the sedimentation velocity. Since the density of each species is known we can determine the radii of each component in the sum, and hence we can calculate the G factor for each of the components in (10). In this way we can determine the quantity $S_j$, where $$S_j = \Delta\rho^1 \zeta^1 \phi_j^1 G^1 + \Delta\rho^2 \zeta^2 \phi_j^2 G^2 \quad (11)$$

for each component j, where $G^1$ and $G^2$ are the G factors calculated using equation (7) with the radii corresponding to sedimentation velocity $V_j$.

Figure 2:
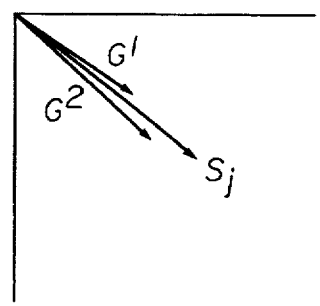
FIG. 2 is an Argand diagram illustrating the relationship between values in a sample calculation.

The quantities $G^1$ and $G^2$ are complex numbers, while the coefficients $\Delta\rho^1 \zeta^1 \phi^1$ and $\Delta\rho^2 \zeta^2 \phi^2$ are real. In principal it should be possible to determine these two coefficients from the complex quantity $S_j$, but in practice this can be difficult if the difference in density between the particles is not substantial. To illustrate this point consider the case when the type 1 particles have a density of 2 g/cc and the type 2 particles have a density of 3 g/cc, and suppose we seek to determine the $\Delta\rho\zeta\phi$ coefficients from the measurement of the quantity $S_j$ for those particles with a sedimentation velocity of 2 μm/s. From equation (2) we find that this sedimentation velocity corresponds to a particle radius of 1 μm for the type 1 particles, and 0.707 μm for the type 2 particles. When we calculate $G^1$ and $G^2$ for these particles using equation (7), we find that the arguments of these two quantities only differ by one degree. The quantities $G^1$, $G^2$, and $S_j$ are illustrated on the Argand diagram shown in FIG. 2.

If $S_j$ is parallel to $G^1$, then $\zeta^2 \phi^2$ must be zero, whereas if $S_j$ is parallel to $G^2$, $\zeta^1 \phi^1$ zero. Thus a small experimental error in $S_j$ can cause large errors in the calculated values of $\zeta^1 \phi^1$ and $\zeta^2 \phi^2$. This sensitivity to experimental error will also be a problem if the particle's density difference is substantial, but the particles are so small that the quantities $G^1$ and $G^2$ are approximately unity. In both these cases it is still possible to determine the individual size distributions using the following procedure, provided the particle species have significantly different zeta potentials.

According to this procedure the sedimentation measurement described above is repeated, but in this case, before the ESA measurements begin, a steady, or slowly-varying electric field is applied across the suspension to bring about an extra displacement of the particles. To avoid confusing this field with the field that drives the ESA pulse, we will refer to the former as the DC field, and call the latter the ESA field. Assuming the zeta potential is the same for all particles of the same species (as is usually the case), then all particles of the same species will be displaced by the same amount under the DC field. Let $d_1$ denote the displacement of the type 1 particles, and let $d_2$ be the displacement of the type 2 particles. The DC field is then turned off and the ESA measurements are made as described above. The contribution to the ESA from those particles with sedimentation velocity $V_j$ will be denoted by $S'_j$, where $$S'_j = \Delta\rho^1 \zeta^1 G^j e^{-i\delta_1} + \Delta\rho^{12} \zeta^{12} G^{2j} e^{-i\delta_2} \quad (12)$$

and $$\delta_j = \frac{\omega d_j}{c} \quad (13)$$

The exponential factors in equation (12) rotate the vectors $G^1$ and $G^2$ by different amounts, so if they were parallel to begin with, they will not be in this second experiment. Thus the equation (12) can be used to accurately determine the values of $\phi_j$, provided the displacements $d_j$ are known.

These displacements are related to the particle $\zeta$ potential by the formula $$d_j = \frac{\epsilon \zeta}{\rho \nu} Et \quad (14)$$

where E is the average DC field strength and t is the time over which the field is applied. In deriving this expression for the displacement we have used the Smoluchowski formula for the DC electrophoretic mobility (see e.g. equation (9.11.19) on p557 of "Foundations of Colloid Science", Vol 2, by R. J. Hunter. Clarendon Press, Oxford 1987)

$$\mu_{DC} = \frac{\epsilon \zeta}{\rho \nu} \quad (15)$$

The first step in the solution to this problem for charge and size is the calculation of the zeta potentials. To determine these quantities we first divide each of the expressions (11) and (12) by $G^1$ and sum over all the sedimentation velocities j.

In this way obtain the formulae:

$$\Delta\rho^1 \Phi^1 \zeta^1 + \Delta\rho^2 X \zeta^2 = \sigma \quad (16)$$

and $$\Delta\rho^1 \Phi^1 e^{-i\delta_1} \zeta^1 + \Delta\rho^2 X e^{-i\delta_2} \zeta^2 = \sigma' \quad (17)$$

where $$\sigma = \sum_j \frac{S_j}{G^1}, \quad \sigma' = \sum_j \frac{S_j}{G^1}, \quad (18)$$

and $$X = \sum_j \phi_j^2 \frac{G^2}{G^1} \quad (19)$$

The unknowns in equations (15) and (16) are $\zeta^1$, $\zeta^2$ and X. On eliminating X from the two equations we get $$e^{-i\delta_2} = \frac{\sigma' - \zeta^1 e^{-i\delta_1}}{\sigma - \zeta^1} \quad (20)$$

By using the fact that the magnitude of the left side of equation (20) is one we obtain an equation involving the single unknown $\zeta^1$:

$$\frac{|\sigma'|^2 - 2\zeta^1 |\sigma'| \cos(\Phi' + \delta_1) + (\zeta^1)^2}{|\sigma|^2 - 2\zeta^1 |\sigma| \cos(\Phi + \delta_1) + (\zeta^1)^2} = 1 \quad (21)$$

where $\Phi = \arg(\sigma)$ and $\Phi' = \arg(\sigma')$. The equation (21) can be solved for $\zeta^1$ by one of the standard numerical root-solving techniques, such as Newton's Method (see e.g. Chapter 5 of "Numerical Methods" by R. Hornbeck. Quantum Publishers Inc., New York 1975). Once $\zeta^1$ is known, $\zeta^2$ can be determined from equation (20). The size distributions of $\Phi^1 j$ and $\Phi^2 j$ can then be determined from the expression (12) for $S_j$.

This method will only work if the factors $\exp(-\delta_j)$ in (12) rotate the G vectors so that they are no longer nearly parallel. The amount of rotation required depends on the accuracy of the ESA measurements. If the measurements are made to 1% accuracy, a 10 degree rotation in the G vectors will suffice. Thus we require the $\delta_j$ factors to differ by around 0.1. If the ESA signal is measured at 1 MHz, this requirement is satisfied if the particle displacements differ by more than 25 µm, where we have used the formula (13) to calculate the displacement from $\delta_j$. If the particle species have zeta potentials of 25 mV and 50 mV, such a displacement would occur under a DC field of 1000 V/m at a time of about 1 second, where we have used the Smoluchowski formula (15) to calculate the particle electrophoretic velocity.

Figure 3:
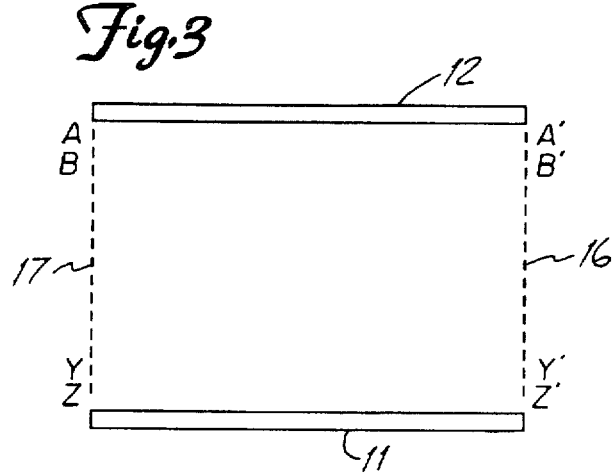
FIG. 3 illustrates schematically a modified electrode arrangement.

There may be practical difficulties that arise in applying such a field, for the field drives electrolyte charge down onto the electrode, where it forms a diffuse layer, shielding the electrode and eventually reducing the applied field on the suspension to zero. The time required for this effect to become substantial depends on the electrode spacing and surface area. One standard way of increasing the time required for polarization to occur is to use platinum black electrodes, since these have a rough surface with a very large surface area (see e.g. p43 of "The Principles of Electrochemistry" by Duncan A MacInnes, Dover Publications New York 1961) Another way to overcome this effect is to use an electrode array such as that shown in FIG. 3.

The top and bottom electrodes 11,12 are used to apply the DC field and the ESA voltage pulse, and are identical in function to those in FIG. 1. The vertical lines on the sides of the cell represent two arrays 16, 17 of small plate-like electrodes, one on each side of the cell. The DC field is first applied to the top and bottom electrodes to bring about the particle displacements, as described above.

During this stage the side electrodes are disconnected. Once the polarization has become a problem, the top and bottom electrodes are switched to ground and at the same time the electrodes A, A' and Z, Z' are connected to the applied voltage source (with voltages of opposite polarity) so that current from the top electrodes flows to A—A' and current from the bottom electrodes flows to Z—Z'. Then these electrodes and the neighbouring electrodes B—B' and Y—Y' are turned on. In this way the polarization charge is removed from the top and bottom electrodes and passed down the side electrodes, until the positive and negative charges meet at the midpoint electrodes and cancel. This cycle of applied voltage and discharge can be repeated to bring about the particle displacements required for size and zeta determination.

In the case when there is only one type of particle but the $\zeta$ potential depends on the particle radius, the size and $\zeta$ distribution can be determined by measuring the ESA spectrum with and without the DC field displacements. From the measurement of the ESA without the DC field we get $\zeta^j \Phi^j$ for each size group j. Then from the change in phase of the jth ESA component after applying the field we get the factor $\delta_j$, which give $\zeta_j$, and hence $\phi^j$ can be determined.

In the above discussion it has been assumed that the suspension contains only two species of particle. If there are more than two species it will be necessary to apply the DC field more than once to bring about different controlled displacements. Each application of the field and subsequent ESA measurement provides another equation and allows us to determine another unknown size and zeta distribution.

In describing this method for determining particle size and $\zeta$ distributions from electroacoustic measurements we have cited the example of a parallel plate ESA apparatus. The method can also be implemented using any other electroacoustic effect and with a great variety of device geometries. To illustrate the possibility of other electroacoustic measurements, suppose a parallel plate device of the form shown in FIG. 1 is set up to measure the CVP rather than the ESA. In this case the voltage pulse is applied to the transducer on the top block rather than across the electrodes. This causes the transducer to generate a soundwave pulse that travels down the block and into the suspension. When the sound wave crosses the interface between the clear liquid and the suspension it generates a voltage between the two electrodes. This voltage is the CVP. From the solution of the electroacoustic equations derived in O'Brien's 1990 paper (Journal of Fluid Mechanics, 212, 81) we find that the Fourier Transform of the CVP pulse $V(\omega)$, is given by:

$$V(\omega) = B \Delta \rho \frac{P_a(\omega)}{K^*(\omega)} \mu_D(\omega) e^{\frac{-i\omega V t}{c}} \quad (22)$$

in the case of a single component monodisperse suspension. Here B is a device constant, K* is the complex conductivity of the suspending liquid, and $P_a(\omega)$ is the Fourier transform of the applied pressure pulse. Comparing this expression with the corresponding formula (4) for the ESA we see that both signals depend in exactly the same way on the dynamic mobility and sedimentation velocity. Thus the analysis that we have described for the ESA can be applied directly to the CVP case.

The procedure that we have described above for extracting the size distributions and $\zeta$ potentials from the measured electroacoustic signals involves a Fourier Analysis of signals, that is it involves the step of determining each of the harmonic components of the ESA signal as a function of time. This is not the only way to extract the size information, however.

To illustrate a possible alternative procedure consider first the case of a single species suspension with a range of particle sizes. In that case the signal $P(\omega)$ varies with time in accordance with the formula (8). If this signal is measured over a range of frequencies at each instant, the resulting "electroacoustic spectrum" (that is, the set of P values over the applied frequencies) can be used to obtain information about $\zeta$ and the size distribution as described in the applicants earlier patent (referred to above). For the case of a two species suspension however, the signal is given by the formula (10), and there are now too many unknowns to permit the determination of the individual size distributions and $\zeta$ potentials. If however we measure the variation of the electroacoustic spectrum with time as a result of the applied force (such as gravity) we obtain additional information that can be used to extract the $\zeta$'s and size distributions for the separate species. The point is that each measurement provides additional information without introducing any more unknowns since the signal from each particle size group varies in a known way with time. Thus one could for instance measure the spectrum at 100 equi-spaced time intervals and then use a computer to adjust the unknown quantities $\zeta^1 \phi_j^1 \Delta \rho 1$ and $\zeta^2 \phi_j^2 \Delta \rho^2$ to minimise the total square error between the measured electroacoustic spectra and the theoretical spectra obtained using equations (6), (7) and (10).

It will be appreciated that variations and additions are possible within the spirit and scope of the invention.

I claim:

1. A method for determining the particle charge and size distributions of particles suspended in a liquid medium comprising:

subjecting the suspension to at least one steady or slowly varying force which moves the particles at a rate that depends on their radius or charge and thereby sets up spatial inhomogeneities in the suspension;

applying at least one of an unsteady electric field and an unsteady mechanical force to the suspension to accelerate the particles, the application of an unsteady electric field resulting in an acoustic wave response being generated by the particles and the application of an unsteady mechanical force resulting in an electrical response being generated by the particles;

measuring the generated response;

monitoring the change in these measurements with time due to the evolution of the spatial inhomogeneities in the suspension; and calculating the particle size and charge distributions for the particles.

2. A method according to claim 1, wherein the calculating step includes determining the contribution to the measured response from each group of particles having the same motion under the influence of the at least one steady or slowly varying force, and calculating the particle size distribution from the determined contribution of each group.

3. A method according to claim 2, wherein the steady force in the subjecting step is gravity.

4. A method according to claim 1, wherein the steady force in the subjecting step is gravity.

5. A method for determining the particle charge and size distributions of particles suspended in a liquid medium, said particles belonging to at least two different species, comprising the steps of:

subjecting the suspension to at least one steady or slowly varying force which moves the particles at a rate that depends on their radius or charge and thereby sets up spatial inhomogeneities in the suspension;

applying at least one of an unsteady electric field and an unsteady mechanical force to the suspension to accelerate the particles, the application of an unsteady electric field resulting in an acoustic wave response being generated by the particles and the application of an unsteady mechanical force resulting in an electrical response being generated by the particles;

measuring the generated response;

monitoring the change in these measurements with time due to the evolution of the spatial inhomogeneities in the suspension; and calculating the particle size and charge distributions for each species.

6. A method according to claim 5, wherein the calculating step includes determining the contribution to the measured response from each group of particles having the same motion under the influence of the at least one steady or slowly varying force, and calculating the particle size distribution from the determined contribution of each group.

7. A method according to claim 6, wherein the steady force in the subjecting step is gravity.

8. A method according to claim 5, wherein the steady force in the subjecting step is gravity.

9. A device for determining the particle charge and size distributions of particles suspended in a liquid medium, said particles belonging to at least two different species, comprising:

a receptacle for receiving a sample of a suspension for measurement;

means for subjecting the suspension to at least one steady or slowly varying force which moves the particles at a rate that depends on their radius or charge and thereby sets up spatial inhomogeneities in the suspension;

means for accelerating the particles in the suspension by applying at least one of an unsteady electric field which results in an acoustic wave response being generated by the particles, and an unsteady mechanical force which results in an electrical response being generated by the particles;

sensor means for measuring the generated response;

means for monitoring the change in these measurements with time due to the evolution of the spatial inhomogeneities in the suspension; and processing means for calculating the particle size and charge distributions for each species.

10. A device according to claim 9, wherein said processing means is adapted to determine the contribution to the measured response from each group of particles having the same motion under the influence of the at least one steady or slowly varying force, and to calculate the particle size distribution from the determined contribution of each group.

11. A device according to claim 10, wherein the means for subjecting comprises an arrangement in which the particles sediment under gravity.

12. A device according to claim 9, wherein the means for subjecting comprises an arrangement in which the particles sediment under gravity.

13. A device for determining the particle charge and size distributions of particles suspended in a liquid medium, comprising:

a receptacle for receiving a sample of a suspension for measurement;

means for subjecting the suspension to at least one steady or slowly varying force which moves the particles at a rate that depends on their radius or charge and thereby sets up spatial inhomogeneities in the suspension;

means for accelerating the particles in the suspension by applying at least one of an unsteady electric field which results in an acoustic wave response being generated by the particles, and an unsteady mechanical force which results in an electrical response being generated by the particles;

sensor means for measuring the generated response;

means for monitoring the change in these measurements with time due to the evolution of the spatial inhomogeneities in the suspension; and processing means for calculating the particle size and charge distributions for the particles.

14. A device according to claim 13, wherein said processing means is adapted to determine the contribution to the measured response from each group of particles having the same motion under the influence of the at least one steady or slowly varying force, and to calculate the particle size distribution from the determined contribution of each group.

15. A device according to claim 14, wherein the means for subjecting comprises an arrangement in which the particles sediment under gravity.

16. A device according to claim 13, wherein the means for subjecting comprises an arrangement in which the particles sediment under gravity.

17. A method for determining the particle charge distribution of particles suspended in a liquid medium comprising:

subjecting the suspension to at least one steady, or slowly varying force which moves the particles at a rate that depends on their charge and thereby sets up spatial inhomogeneities in the suspension;

applying at least one of an unsteady electric field and an unsteady mechanical force to the suspension to accelerate the particles, the application of an unsteady electric field resulting in an acoustic wave response being generated by the particles and the application of an unsteady mechanical force resulting in an electrical response being generated by the particles;

measuring the generated response;

monitoring the change in these measurements with time due to the evolution of the spatial inhomogeneities in the suspension; and calculating the particle charge distribution for the particles.

18. A method according to claim 17, wherein the steady force in the subjecting step is gravity.

19. A method according to claim 17, wherein the particles in the liquid medium belong to at least two different species and the particle charge distribution is calculated for each species.

20. A method for determining the particle size distribution of particles suspended in a liquid medium comprising:

subjecting the suspension to at least one steady or slowly varying force which moves the particles at a rate that depends on their radius and thereby sets up spatial inhomogeneities in the suspension;

applying at least one of an unsteady electric field and an unsteady mechanical force to the suspension to accelerate the particles, the application of an unsteady electric field resulting in an acoustic wave response being generated by the particles and the application of an unsteady mechanical force resulting in an electrical response being generated by the particles;

measuring the generated response;

monitoring the change in these measurements with time due to the evolution of the spatial inhomogeneities in the suspension; and calculating the particle size distribution for the particles.

21. A method according to claim 20, wherein the calculating step includes determining the contribution to the measured response from each group of particles having the same motion under the influence of the at least one steady or slowly varying force, and calculating the particle size distribution from the determined contribution of each group.

22. A method according to claim 20, wherein the steady force in the subjecting step is gravity.

23. A method according to claim 20, wherein the particles in the liquid medium belong to at least two different species and the particle size distribution is calculated for each species.

* * * * *

UNITED STATES PATENT AND TRADEMARK OFFICE
CERTIFICATE OF CORRECTION

PATENT NO. : 5,616,872
DATED : APRIL 1, 1997
INVENTOR(S) : RICHARD W. O'BRIEN

It is certified that error appears in the above-indentified patent and that said Letters Patent is hereby corrected as shown below:

Col. 6, line 13, delete "$\omega$", insert --$\zeta$--

Col. 6, line 33, delete "$\omega$", insert --$\zeta$--

Col. 7, line 43, before word "zero", insert --is--

Signed and Sealed this

Twenty-third Day of September, 1997

Attest:

BRUCE LEHMAN

Attesting Officer

Commissioner of Patents and Trademarks